US010794831B2

United States Patent
Ota

(10) Patent No.: US 10,794,831 B2
(45) Date of Patent: Oct. 6, 2020

(54) ORGANIC COMPOUND ANALYZER, ORGANIC COMPOUND ANALYSIS METHOD, AND PROGRAM FOR ORGANIC COMPOUND ANALYZER

(71) Applicant: HORIBA, Ltd., Kyoto-shi, Kyoto (JP)

(72) Inventor: Chikashi Ota, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 16/325,354

(22) PCT Filed: Aug. 8, 2017

(86) PCT No.: PCT/JP2017/028757
§ 371 (c)(1),
(2) Date: Feb. 13, 2019

(87) PCT Pub. No.: WO2018/034205
PCT Pub. Date: Feb. 22, 2018

(65) Prior Publication Data
US 2019/0204230 A1    Jul. 4, 2019

(30) Foreign Application Priority Data
Aug. 18, 2016    (JP) .................................. 2016-160638

(51) Int. Cl.
| | | |
|---|---|---|
| G01J 3/44 | (2006.01) | |
| G01N 21/65 | (2006.01) | |
| G01N 33/483 | (2006.01) | |
| G16C 20/30 | (2019.01) | |
| G16C 20/40 | (2019.01) | |
| G16C 20/70 | (2019.01) | |

(52) U.S. Cl.
CPC .......... *G01N 21/65* (2013.01); *G01N 33/483* (2013.01); *G16C 20/30* (2019.02); *G16C 20/40* (2019.02); *G16C 20/70* (2019.02)

(58) Field of Classification Search
CPC ...... G01N 21/65; G01N 33/483; G16C 20/30; G16C 20/40; G16C 20/70
See application file for complete search history.

(56) References Cited

U.S. PATENT DOCUMENTS

| | | | | |
|---|---|---|---|---|
| 10,565,474 B2* | 2/2020 | Otsuka | ............... | G06K 9/00127 |
| 2004/0073120 A1* | 4/2004 | Motz | .................... | A61B 5/0071 |
| | | | | 600/478 |
| 2015/0168292 A1 | 6/2015 | Otsuka | | |

FOREIGN PATENT DOCUMENTS

| | | |
|---|---|---|
| JP | 2011174906 A | 9/2011 |
| JP | 5649825 B2 | 11/2014 |

OTHER PUBLICATIONS

B. Yuan, et al; Temperature-dependent near-infrared spectra of bovine serum albumin in aqueous solutions: spectral analysis by . . . ; Applied Spectroscopy; vol. 57; No. 10, 2003; pp. 1223-1229.

(Continued)

*Primary Examiner* — Tarifur R Chowdhury
*Assistant Examiner* — Jonathon Cook
(74) *Attorney, Agent, or Firm* — Lucas & Mercanti, LLP

(57) ABSTRACT

An organic compound analyzer is provided which is capable of highly accurately determining a denaturation feature point on which a minute structural change of an organic compound is reflected. The organic compound analyzer includes an actual measured data storage section, an evaluation criterion vector setting section, a score calculation section, and a change feature point determination section. The actual measured data storage section is configured to store in pairs a plurality of actual measured spectra obtained through measurement of a sample containing an organic compound under a plurality of different external stimulus conditions, and external stimulus conditions under which spectra are respectively measured. The evaluation criterion vector setting section is configured to set a loading that indicates weighting to individual wavenumbers at which the spectra are measured. The score calculation section is configured to calculate a score corresponding to the loading for each of external simulation conditions under which the spectra are measured, on the basis of the loading and the actual mea- (Continued)

sured data. The change feature point determination section is configured to calculate a denaturation temperature of the organic compound on the basis of a change in the score with respect to external stimulus conditions.

9 Claims, 9 Drawing Sheets

(56) References Cited

OTHER PUBLICATIONS

A. Uda, et al; Principal component analysis for quality control; PDA Journal of GMP and validation in Japan; vol. 8; No. 2; 2006; pp. 94-105.

C. Ota, et al; Assessment of the protein-protein interactions in a highly concentrated antibody solution by using raman spectroscopy; Pharmaceutical Research; vol. 33; Issue 4; 2015; pp. 956-969.

International Search Report dated Oct. 31, 2017 for PCT/JP2017/028757 and English translation.

EPO, Extended European Search Report for the corresponding European patent application No. 17841430.6, dated Mar. 6, 2020.

Pengfei Zhang et al., "Characterization of Single Heat-activated Bacillus Spores Using Laser Tweezers Raman Spectroscopy," Optics Express, Sep. 14, 2009, pp. 16480-16525, vol. 17, No. 19.

Chikashi Ota et al., "The Molecular Interaction of a Protein in Highly Concentrated Solution Investigated by Raman Spectroscopy : The Molecular Interaction of a Protein", Bliopolymers, Nov. 22, 2014, pp. 237-246, vol. 103, No. 4.

* cited by examiner

ORGANIC COMPOUND ANALYZER, ORGANIC COMPOUND ANALYSIS METHOD, AND PROGRAM FOR ORGANIC COMPOUND ANALYZER

CROSS REFERENCE TO RELATED APPLICATION

This Application is a 371 of PCT/JP2017/028757 filed on Aug. 8, 2017 which, in turn, claimed the priority of Japanese Patent Application No. 2016-160638 filed on Aug. 18, 2016, both applications are incorporated herein by reference.

TECHNICAL FIELD

The present invention relates to an organic compound analyzer that analyzes an organic compound on the basis of a spectrum. The present invention also relates to an organic compound analysis method and a program for an organic compound analyzer.

BACKGROUND ART

In order to perform concentration estimation of an organic compound, such as protein, contained in a sample, a technique for multivariate analysis (chemometrics) has conventionally been employed which includes measuring a spectrum of the sample (for example, Raman spectrum or infrared absorption spectrum), and handling, as a variable, spectrum intensity information about a full wavenumber region of the spectrum (refer to Patent Document 1).

In order to measure a denaturation temperature that is an important index for analyzing a structure of protein, infrared absorption spectrum measurement is carried out while subjecting a sample containing the protein to temperature change. For example, spectrum intensity is measured at an infrared absorption peak derived from the structure of the protein after being modified, while subjecting the sample to temperature change. An approximately intermediate temperature between a temperature at which spectrum intensity starts to increase, and a temperature at which the spectrum intensity remains unchanged is used as a denaturation temperature.

PRIOR ART DOCUMENT

Patent Document

Patent Document 1: Japanese Patent No. 5649825

SUMMARY OF THE INVENTION

Problems to be Solved by the Invention

With the conventional analysis method using a spectrum, it is however difficult to capture a minute structural change that seems to occur at an early stage of thermal denaturation, and a denaturation temperature corresponding to the change.

It is therefore difficult to achieve high-level of quality management in, for example, an antibody drug whose effect may be significantly affected by the minute structural change.

The present invention has been made in view of the above problem, and has for its main object to provide an organic compound analyzer, an organic compound analysis method, and a program for an organic compound analyzer, which make it possible to highly accurately determine, for example, a thermal denaturation temperature on which a minute structural change in the early stage of thermal denaturation of protein is reflected.

Means of Solving the Problems

Specifically, an organic compound analyzer in the present invention includes an actual measured data storage section, an evaluation criterion vector setting section, a score calculation section, and a change feature point determination section. The actual measured data storage section is configured to store in pairs a plurality of actual measured spectra obtained through measurement of a sample containing an organic compound under a plurality of different external stimulus conditions, and external stimulus conditions under which actual measured spectra are respectively measured. The evaluation criterion vector setting section is configured to set an evaluation criterion vector having a number of elements equal to a number of measurement points for a wavenumber at which spectrum intensity of the actual measured spectra is measured. The score calculation section is configured to calculate a score based on an inner product of the actual measured spectra and the evaluation criterion vector with respect to a plurality of external stimulus conditions. The change feature point determination section is configured to determine a change feature point of the organic compound on the basis of a change in the score with respect to external stimulus conditions.

An organic compound analysis method in the present invention is intended to analyze an organic compound on the basis of a plurality of actual measured spectra obtained through measurement of a sample containing an organic compound under a plurality of different external stimulus conditions, and external stimulus conditions under which actual measured spectra are respectively measured. The method includes an evaluation criterion vector setting step, a score calculation step, and a change feature point determination step. The evaluation criterion vector setting step is to set an evaluation criterion vector having a number of elements equal to a number of measurement points for a wavenumber at which spectrum intensity of the actual measured spectra is measured. The score calculation step is to calculate a score based on an inner product of the actual measured spectra and the evaluation criterion vector with respect to a plurality of external stimulus conditions. The change feature point determination step is to determine a change feature point of the organic compound on the basis of a change in the score with respect to external stimulus conditions.

The term "a plurality of different external stimulus conditions" denotes parameters of identical type that are different in frequency and quantity.

With the above configurations, a change feature point of an organic compound is determined on the basis of a change in the score obtained through evaluation of a measured actual measured spectrum by being weighted on each wavenumber, with respect to external stimulation conditions. It is therefore possible to determine the change feature point by adding spectrum intensity information over the entire wavenumber region.

Thus, when an organic compound is protein, a spectrum change derived from a micro structural change in an early stage of denaturation which occurs in anywhere other than a peak of an actual measured spectrum can be reflected on a denaturation temperature that is a change feature point.

This leads to a highly accurate calculation of the denaturation temperature derived from the structural change smaller than the denaturation temperature conventionally calculated on the basis of a change in spectrum intensity in a single peak.

In order to set the evaluation criterion vector being appropriate on the basis of a large number of actual measured spectrum data, the evaluation criterion vector setting section needs to set the evaluation criterion vector by performing multivariate analysis of a spectral matrix composed of a plurality of actual measured spectra measured under a plurality of different external stimulus conditions.

The following configurations are suitable for performing a proper analysis on the basis of only actually measured data even when it is unknown whether a spectrum is affected by a minute structural change that may occur due to an organic compound contained in a sample or external stimulus conditions, and it is unclear what type of evaluation criterion vector needs to be set. That is, the evaluation criterion vector setting section needs to set the evaluation criterion vector by calculating one or a plurality of PCA loadings on the basis of a spectral matrix composed of a plurality of actual measured spectra measured under a plurality of different external stimulus conditions. The score calculation section needs to calculate a product of the spectral matrix and the PCA loading as the score under a plurality of external stimulus conditions. Specifically, with a technique of PCA (Principal Component Analysis), an evaluation axis suitable for describing a spectrum distribution is automatically settable without setting an evaluation criterion vector from a known spectrum.

In order to calculate the score on which a minute structural change in the early stage of denaturation is reflected so as to accurately calculate a denaturation temperature derived from the minute structural change, the evaluation criterion vector setting section needs to set the evaluation criterion vector by calculating PCA loadings having second and subsequent contribution rates on the basis of the spectral matrix. The change feature point determination section needs to determine a change feature point on the basis of a change in the score corresponding to PCA loadings having the second and subsequent contribution rates calculated by the score calculation section, with respect to external stimulus conditions. For example, when an organic compound is protein, a PCA loading having the highest contribution rate mainly reflects a spectrum of the protein before denaturation. Therefore, only the influence of the protein after a minute structural change and denaturation is highly likely to occur in the PCA loadings respectively having the second and subsequent contribution rates. The use of this tendency makes it possible to extract only the minute structural change from the score. Even in the case of an organic compound other than protein, it becomes possible to extract minute structural change and composition change occurred in the organic compound.

For example, it is assumed that a spectrum derived from a structural change occurred in an organic compound due to a change in external stimulus conditions is known. In order to make it easier for the structural change to occur in a score, the evaluation criterion vector setting section needs to set the evaluation criterion vector on the basis of a known spectrum of the organic compound. The score calculation section needs to calculate a product of a spectral matrix composed of a plurality of actual measured spectra measured under a plurality of different external stimulus conditions and the evaluation criterion vector, as the score under a plurality of external stimulus conditions.

In order to accurately determine a change feature point, for example, even when an organic compound in a sample has such a high concentration that little or no light irradiated onto the sample passes through, the spectrum is a Raman spectroscopy spectrum measured by Raman spectroscopy method. With this configuration, even when a sample has a high concentration at which it is difficult to obtain an infrared absorption spectrum, spectrum intensity is measurable, thus making it possible to analyze a denaturation temperature even for high-concentration samples.

When the organic compound is an antibody and the sample is an antibody drug, it is possible to achieve a high-level of quality management in which a minute structural change can be evaluated by applying the present invention.

In order to analyze, for example, different denaturations of proteins, the external stimulus condition needs to be either one of a concentration and a pH of a solute added to a sample, existence time of the sample in an interface, and a temperature.

The following configurations are suitable for enhancing calculation accuracy of a denaturation temperature due to a minute structural change by using only data in actual measured data which is obtained during occurrence of a minute structural change due to a temperature change, except for data obtained, for example, after completion of denaturation of protein due to a temperature change. Specifically, when the organic compound is protein and the external stimulation conditions are temperatures, the change feature point determination section needs to include an onset temperature calculation section, a data extraction section, and a denaturation temperature output section. The onset temperature calculation section is configured to calculate an onset temperature at which a component in which denaturation of the protein is already completed starts to occur, on the basis of a change in the score with respect to a temperature which is calculated from a plurality of the actual measured spectra. The data extraction section is configured to extract, from the actual measured data storage section, an actual measured spectrum measured at a lower temperature than the onset temperature. The denaturation temperature output section is configured to calculate a denaturation temperature on the basis of a change in the score with respect to a temperature which is calculated by the score calculation section on the basis of actual measured data extracted by the data extraction section.

In order that a conventional organic compound analyzer is capable of implementing functions similar to those in the present invention, for example, in a retrofit manner, it is necessary to install a program for an organic compound analyzer causing a computer to perform functions into an existing apparatus. The functions correspond to an actual measured data storage section, an evaluation criterion vector setting section, a score calculation section, and a change feature point determination section. The actual measured data storage section is configured to store in pairs a plurality of actual measured spectra obtained through measurement of a sample containing an organic compound under a plurality of different external stimulus conditions, and external stimulus conditions under which actual measured spectra are respectively measured. The evaluation criterion vector setting section is configured to set an evaluation criterion vector having the number of elements equal to the number of measurement points for a wavenumber at which spectrum intensity of the actual measured spectra is measured. The score calculation section is configured to calculate a score based on an inner product of the actual measured spectra and the evaluation criterion vector with respect to a plurality of external stimulus conditions. The change feature point determination section is configured to determine a change feature point of the organic compound on the basis of a change in the score with respect to external stimulus conditions. The program for an organic compound analyzer may be electronically distributed, or alternatively may be stored in a storage medium, such as CD, DVD, HD, and flash memory. In other words, an install operation into a computer may be carried out using the program for an organic compound analyzer.

Effects of the Invention

With the organic compound analyzer in the present invention thus configured, the change feature point is determined on the basis of the score on which the spectrum intensity information for all wavenumbers of a spectrum is reflected. It is therefore possible to highly accurately calculate a denaturation temperature due to a minute structural change in the early stage of denaturation, for example, when an organic compound is protein. Consequently, the minute structural change occurred in the protein is analyzable on the basis of the calculated denaturation temperature or the like.

Figure 1:
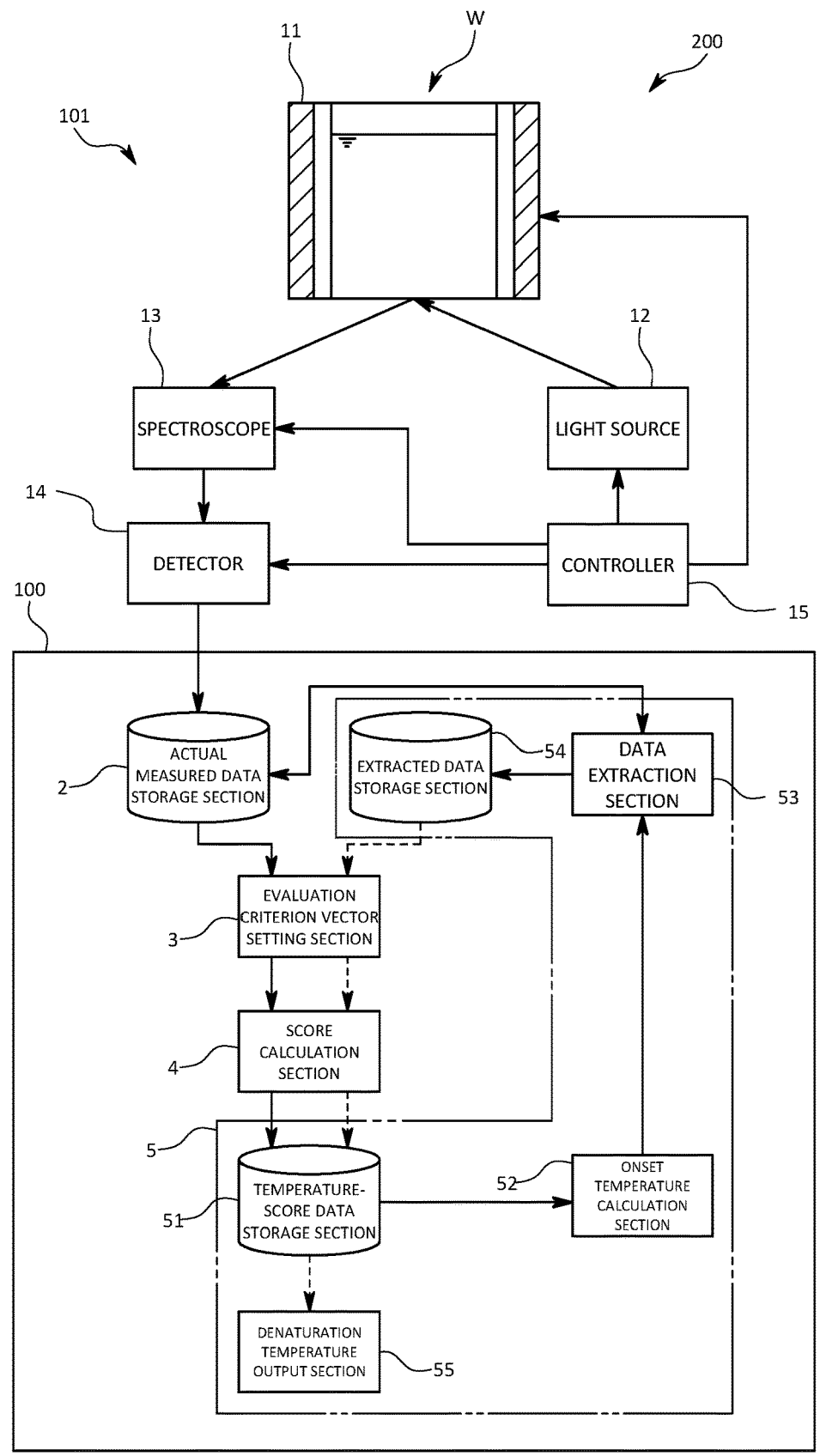
FIG. 1 is a schematic diagram illustrating an organic compound analyzer and an organic compound analysis system in a first embodiment of the present invention.

DESCRIPTION OF THE REFERENCE NUMERAL 100 organic compound analyzer
2 actual measured data storage section
3 evaluation criterion vector setting section
4 score calculation section
5 change feature point determination section
51 temperature-score data storage section
52 onset temperature calculation section
53 data extraction section
54 extracted data storage section
55 denaturation temperature output section Mode for Carrying Out the Invention An organic compound analyzer 100 and an organic compound analysis system 200 in a first embodiment of the present invention are described below with reference to the drawings. The organic compound analysis system 200 in the first embodiment is that is configured to determine a denaturation temperature of a sample W containing protein as an organic compound, on the basis of a spectrum obtained while subjecting the sample W to temperature change. More specifically, the protein is an antibody and the sample W is a solution of an antibody drug. The spectrum is a Ramon spectroscopy spectrum.

As illustrated in FIG. 1, the organic compound analysis system 200 is composed of a measuring apparatus 101 that is configured to measure a Ramon spectroscopy spectrum, and the organic compound analyzer 100 that is configured to calculate a denaturation temperature derived from a micro structural change occurred in the antibody due to the temperature change, on the basis of data obtained by the measuring apparatus 101.

The measuring apparatus 101 includes a light source 12, a spectroscope 13, a detector 14, a heater 11, and a controller. The light source 12 is that is configured to irradiate laser light of a predetermined wavelength to a cell accommodating therein the solution of the antibody drug that is the sample W. The spectroscope 13 is that is configured to split Raman scattering light generated from the sample W by the laser light. The detector 14 is that is configured to detect the Raman scattering light after passing through the spectroscope 13, and is that is configured to output intensity of the Raman scattering light. The heater 11 is that is configured to increase a temperature of the sample W. The controller is that is configured to control the light source 12, the spectroscope 13, the detector 14, and the heater 11.

The controller is configured as follows. The controller performs feedback control so that the sample W reaches a predetermined temperature by the heater 11. The controller causes the light source 12 to emit laser light at a point in time at which it reaches the predetermined temperature. The controller causes the detector 14 to output a Raman spectroscopy spectrum at the above temperature to the organic compound analyzer 100.

The organic compound analyzer 100 is a so-called computer including a CPU, memory, an A/D-D/A converter, and input-output means, such as a display and a keyboard. The organic compound analyzer 100 is that is configured to implement individual functions through cooperation with various devices during execution of a program for the organic compound analyzer 100 stored in the memory. More specifically, the organic compound analyzer 100 performs PCA (primary component analysis) of Raman spectroscopy spectra at different measurement temperatures which are respectively external stimulus conditions measured by the measuring apparatus 101, and determines a denaturation temperature of a minute structural change occurred in the antibody on the basis of a temperature change in a score calculated. In other words, the organic compound analyzer 100 in the first embodiment is configured to fulfill functions as at least an actual measured data storage section 2, an evaluation criterion vector setting section 3, a score calculation section 4, a change feature point determination section 5, and an extracted data storage section 54.

These sections are described in detail below.

The actual data storage section 2 is that is configured to store, as actual measured data, the Raman spectroscopy spectrum that is an actual measured spectrum outputted from the measuring apparatus 101 is paired with a measurement temperature thereof. That is, a Ramon spectroscopy spectrum measured at a certain temperature can be handled as a row vector using, as an element, spectrum intensities in a plurality of Raman shifts. In the present embodiment, individual Raman spectrum intensities are normalized for the PCA and stored in the actual measured data storage section 2 as a spectral matrix in which a plurality of Raman spectroscopy spectra are arranged in ascending order of measurement temperature on a row-by-row basis. Specifically, when Raman spectroscopy spectrum intensity is measured by M point Raman shifts at N measurement temperatures, actual measured data of Raman spectroscopy spectra at individual temperatures are that is configured to be stored as matrix data indicated by the following formula:

$$A = \begin{bmatrix} x_{11} & \cdots & x_{1M} \\ \vdots & \ddots & \vdots \\ x_{N1} & \cdots & x_{NM} \end{bmatrix}$$ [Formula 1]

where A denotes a spectral matrix with N rows and M columns and each row indicates a Raman spectroscopy spectrum at each measurement temperature, and xij denotes Raman spectroscopy spectrum intensity at a measurement temperature $T(i)$ and a Raman shift $RS(j)$. Arrangements are made so that a measurement temperature at which a Raman spectroscopy spectrum is measured decreases with decreasing the value of "i".

Figure 2:
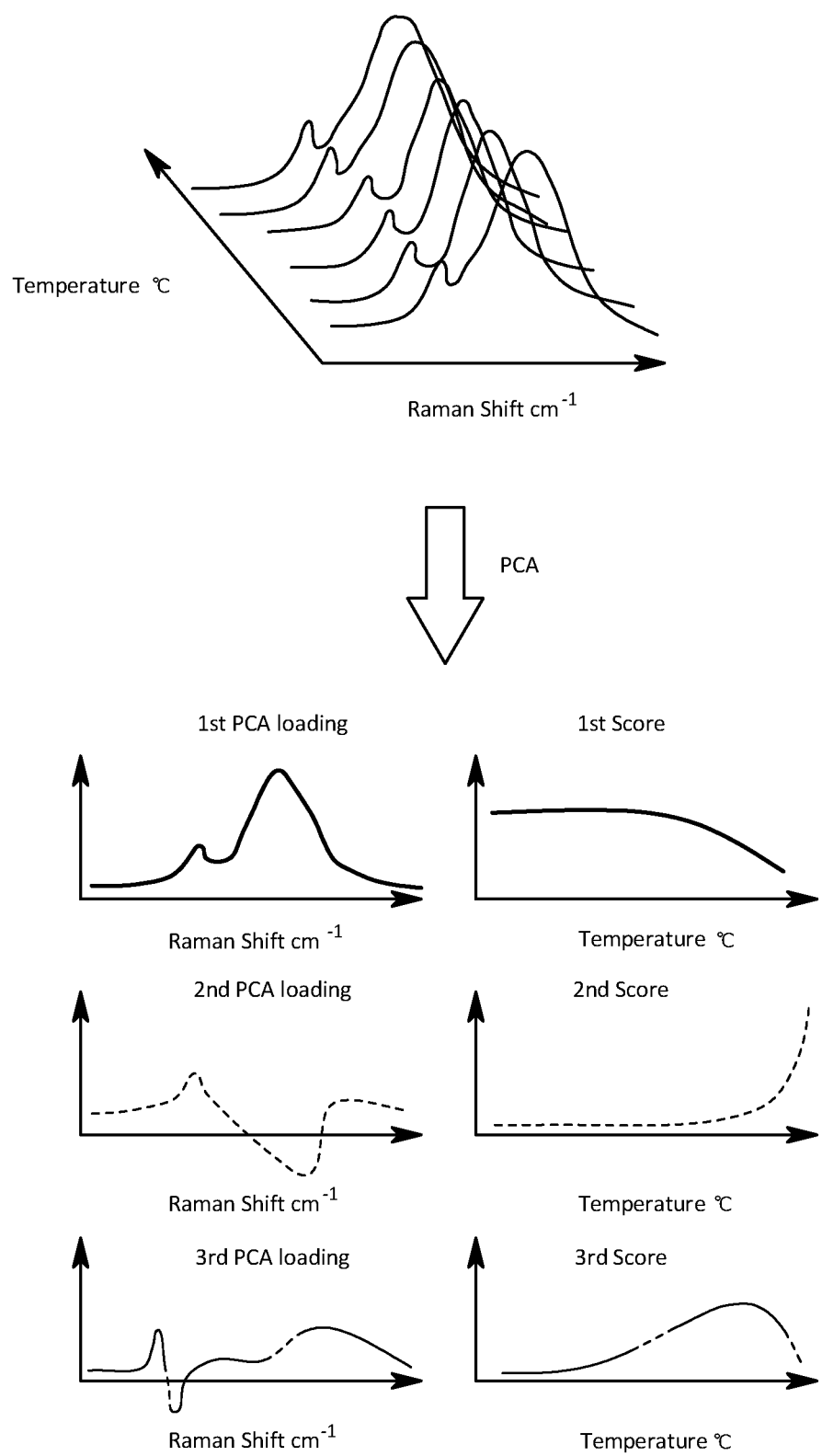
FIG. 2 is a schematic diagram illustrating an analysis image by a PCA with respect to actual measured data in the first embodiment.

The evaluation criterion vector setting section 3 and the score calculation section 4 are that is configured to regulate so-called functions for PCA. More specifically, the evaluation criterion vector setting section 3 is that is configured to set an evaluation criterion vector having the number of elements equal to the number of measurement points for wavenumbers at which spectrum intensity for the actual measured spectrum is measured. With the first embodiment, measured Raman spectroscopy spectra are regarded as superposition of a plurality of reference Raman spectroscopy spectra derived from a plurality of proteins and structures, and the evaluation criterion vector is set so as to represent each reference spectroscopy spectrum. Specifically, with the first embodiment, the evaluation reference criterion vector setting section 3 is that is configured to set evaluation reference vectors by calculating first to third PCA loadings as a PCA loading on the basis of a spectral matrix using, as an element, a Raman spectroscopy spectrum at each measurement temperature as illustrated in FIG. 2. More specifically, when A is a spectral matrix, an inherent vector of a variance-covariance matrix $A^TA$ calculated from a left side of A to a transposed matrix $A^T$ of A is calculated as a PCA loading. That is, the PCA loading is set so that scattering of individual measurement data reaches maximum on the basis of an algorithm of PCA. Here, the PCA loading is expressed as row vector data having the number of elements equal to the number M of Raman shifts after subjected to the measurement. The first PCA loading has a highest contribution rate, followed in order by the second PCA loading and the third PCA loading. With the first embodiment, the first PCA loading can also be considered as a first evaluation axis for evaluating a spectrum obtained after averaging influences of an antibody and all components in the middle of, or after denaturation. The second PCA loading can also be considered as a second evaluation axis for evaluating a spectrum resulting from a component of the antibody whose denaturation is already completed. The third PCA loading can also be considered as a third evaluation axis for evaluating a spectrum resulting from a component of the antibody which is in the middle of minute denaturation.

The score calculation section 4 is that is configured to calculate scores respectively corresponding to the PCA loadings on a temperature basis that is an external stimulation condition under which the Raman spectroscopy spectrum is measured. Each of the scores is a value based on the PCA loadings and the spectral matrix. In still other words, the score is a value that is configured to be evaluable as a one-dimensional quantity by projecting a Raman spectroscopy spectrum that is N-dimensional data measured at each measurement temperature onto a single evaluation axis being set by the PCA loading. First to third scores respectively corresponding to the first to third PCA loadings are calculated in the first embodiment. That is, because these PCA loadings are inherent vectors of the variance-covariance matrix $A^TA$ based on the spectral matrix A, the spectral matrix can be expressed as follows by using the individual scores.

$$A \approx t_1 P_1^T + t_2 P_2^T + t_3 P_3^T$$ [Formula 2]

where $t_i$ denotes a row vector of the number of elements N indicating the i-th score, and $P_i^T$ denotes a transposed matrix of a matrix $P_i$ indicating the i-th PCA loading, and a row vector of the number of elements M. Although being effective up to a third component in the present embodiment, the spectral matrix can also be expressed by a product of a larger number of scores and loadings.

The row vectors respectively indicating the scores can be calculated by multiplying the PCA loadings in order from right by the spectral matrix A as follows.

$$t_i = AP_i$$ [Formula 3]

$$\begin{bmatrix} t_{1i} \\ \vdots \\ t_{Ni} \end{bmatrix} = \begin{bmatrix} x_{11} & \cdots & x_{1M} \\ \vdots & \ddots & \vdots \\ x_{N1} & \cdots & x_{NM} \end{bmatrix} \begin{bmatrix} p_{1i} \\ \vdots \\ p_{Mi} \end{bmatrix}$$

where $t_{ni}$ denotes the i-th score corresponding to the i-th PCA loading $P_i$ in a measurement temperature $TE(n)$ (an integer of $1 \leq n \leq N$).

Thus, the score calculation section 4 is that is configured to calculate the score at each of measurement temperatures on the basis of an inner product of the Raman spectroscopy spectrum and each of the PCA loadings at each of the measurement temperatures. Because the score is calculated one by one as a scalar quantity with respect to each of the measurement temperatures, it is possible to draw a two-dimensional graph of scores calculated on the basis of a measurement temperature at which a Raman spectroscopy spectrum is measured, and the Raman spectroscopy spectrum at the measurement temperature.

The change feature point determination section 5 is that is configured to calculate a denaturation temperature that is a change feature point of the antibody on the basis of a change in the second score or third score corresponding to the second PCA loading or third PCA loading with respect to a temperature. The change feature point determination section 5 in the first embodiment is that is configured to improve calculation accuracy of a final denaturation by calculating a denaturation temperature as a change feature point, and by extracting actual measured data reflecting a state in which denaturation is not yet completed on the basis of the calculated denaturation temperature, so that PCA is repeated again.

More specifically, the change feature point determination section 5 includes a temperature-score data storage section 51, an onset temperature calculation section, a data extraction section 53, an extracted data storage section 54, and a denaturation temperature output section 55.

The temperature-score data storage section 51 is that is configured to store therein temperature-score data in which the first to third scores calculated by the score calculation section 4 are respectively paired with measurement temperatures when Raman spectroscopy spectra used for calculating scores are respectively measured.

Figure 3:
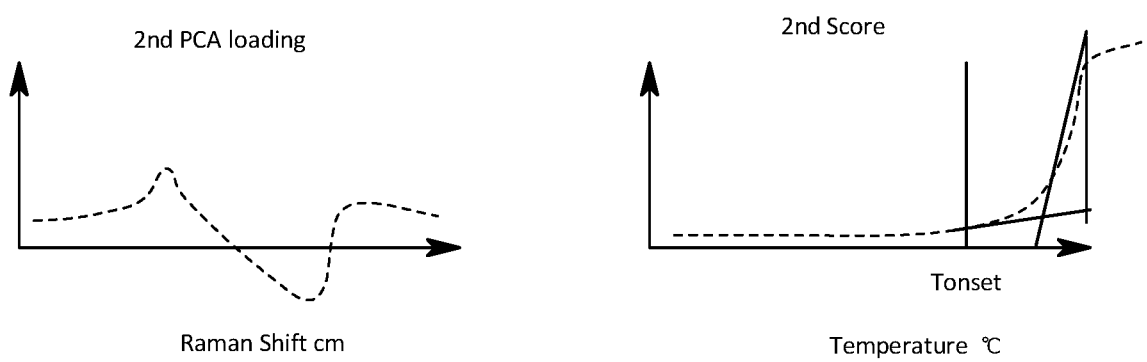
FIG. 3 is a schematic diagram illustrating a calculation procedure for an offset temperature on the basis of a temperature change of a second score in the first embodiment.

The onset temperature calculation section 52 is that is configured to calculate an onset temperature that is a temperature at which a component of the antibody whose denaturation is already completed starts to occur, on the basis of a change in the second score with respect to a temperature which is calculated from the second PCA loading for evaluating a spectrum of a component whose denaturation is already completed, which is already calculated from the actual measured data. For example, the onset temperature calculation section 52 is that is configured to search a termination point of a state in which the second score is maintained at a certain value as illustrated in a temperature change graph for the second score in FIG. 3, and is that is configured to output a temperature at that point as an onset temperature. For example, the onset temperature calculation section 52 is that is configured to output, as an onset temperature, a temperature at which a difference or ratio between adjacent scores values exceeds a predetermined value when the second scores are arranged in ascending order of temperatures.

Figure 4:
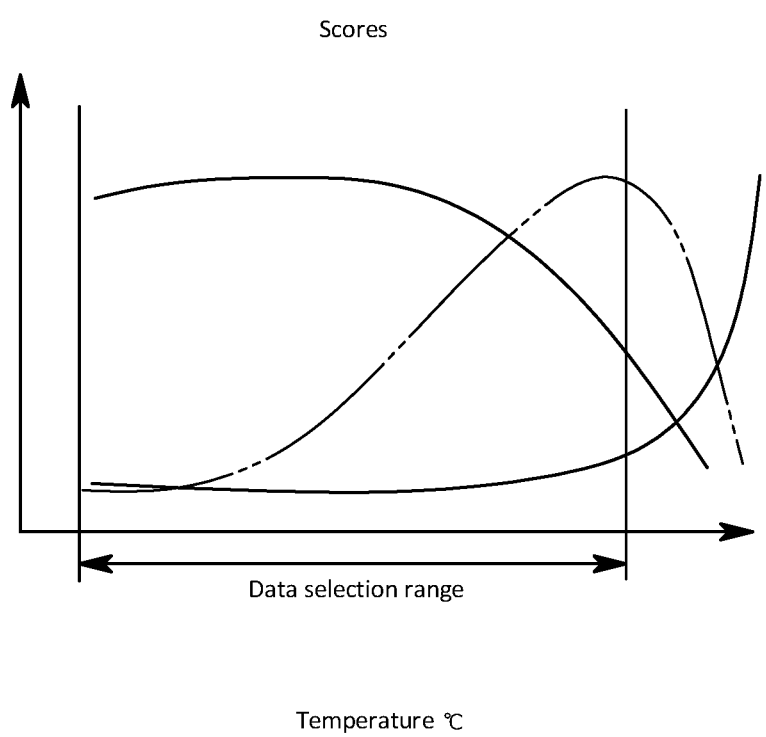
FIG. 4 is a schematic diagram illustrating an extracted temperature region of actual measured data in the first embodiment.

The data extraction section 53 is that is configured to extract, as extracted data, actual measured data containing a Raman spectroscopy spectrum measured at a lower temperature than the offset temperature obtained from the second score in the actual measured data storage section 2. That is, the data extraction section 53 extracts only data of Raman spectroscopy spectra belonging to a region from a point before denaturation starts to the onset temperature obtained from the second score as illustrated in FIG. 4. For example, the data extraction section 53 extracts Raman spectroscopy spectra other than Raman spectroscopy spectra which are measured at higher temperatures than the onset temperature, and are indicated by dotted line as illustrated in an image of Raman spectroscopy spectra in FIG. 5.

Figure 5:
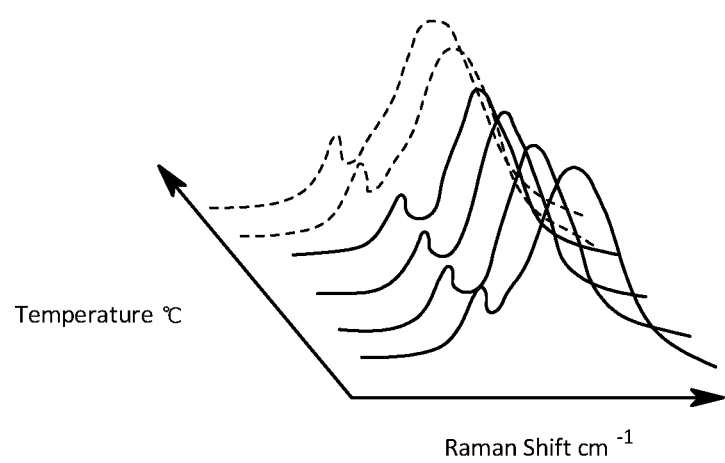
FIG. 5 is a schematic diagram illustrating analysis image by PCA with respect to extracted data in the first embodiment.

The extracted data storage section is that is configured to store extracted data extracted by the data extraction section 53. As illustrated in FIG. 5, the Raman spectroscopy spectra being stored in the extracted data storage section are again subjected to PCA by the evaluation criterion vector setting section 3 and the score calculation section 4, thereby recalculating the first score, the second score, and the third score.

The denaturation temperature output section 55 is that is configured to calculate a denaturation temperature on the basis of a change in the third score with respect to temperature which is calculated from the extracted data by the score calculation section 4.

Figure 6:
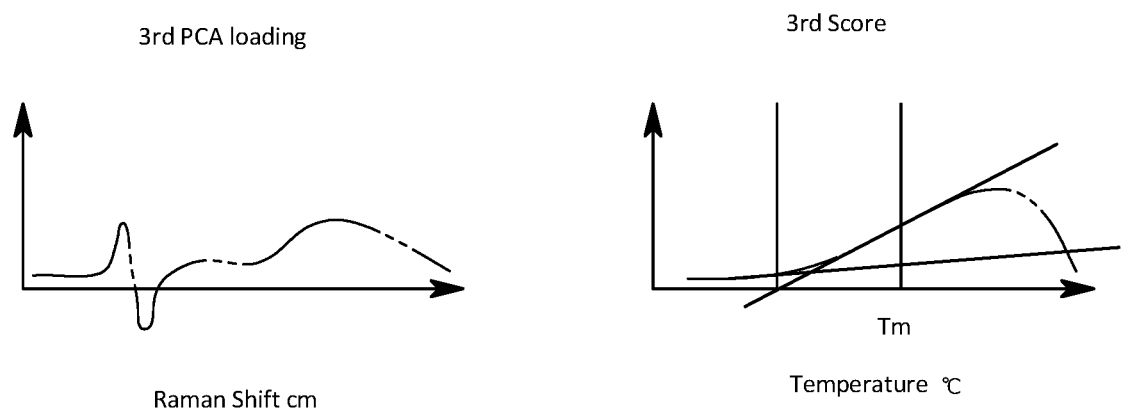
FIG. 6 is a schematic diagram illustrating a calculation procedure for a denaturation temperature on the basis of a temperature change of a third score in the first embodiment.

For example, the denaturation temperature output section 55 is that is configured to detect an onset temperature being a temperature at which it starts to increase from the certain value with increasing temperature in the third score, and a denaturation termination temperature being a temperature of extreme value at which the denaturation is terminated and the third score stops increasing and then decreases again as illustrated in FIG. 6. Thereafter, the denaturation temperature output section 55 is that is configured to output, as a denaturation temperature, a midpoint temperature of the onset temperature and the denaturation termination temperature. Alternatively, the denaturation temperature output section 55 may be that is configured to calculate a denaturation temperature on the basis of the second score. For example, as illustrated in FIG. 4, the denaturation temperature output section 55 may be that is configured to operate by using, as a denaturation termination temperature, a location where values are saturated and reach an approximately certain value in the second score, and by using, as an onset temperature, a point from which the score starts to increase, thereby using a midpoint temperature therebetween as a denaturation temperature.

Figure 7:
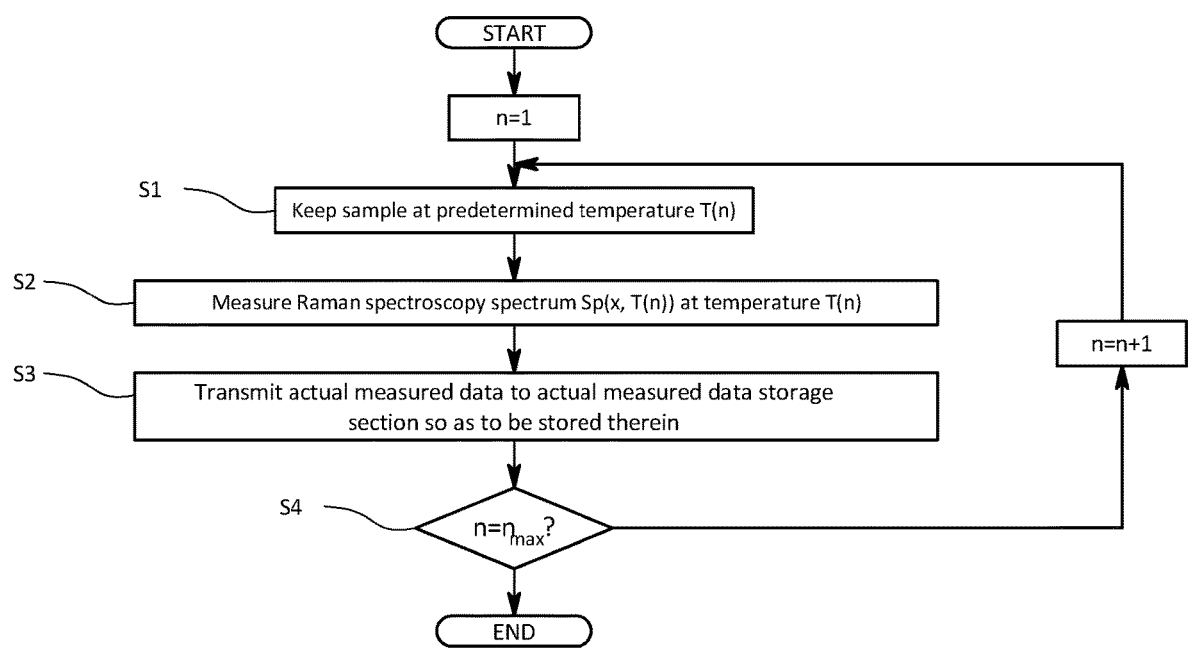
FIG. 7 is a flowchart illustrating a measurement procedure for actual measured data in the first embodiment.
Figure 8:
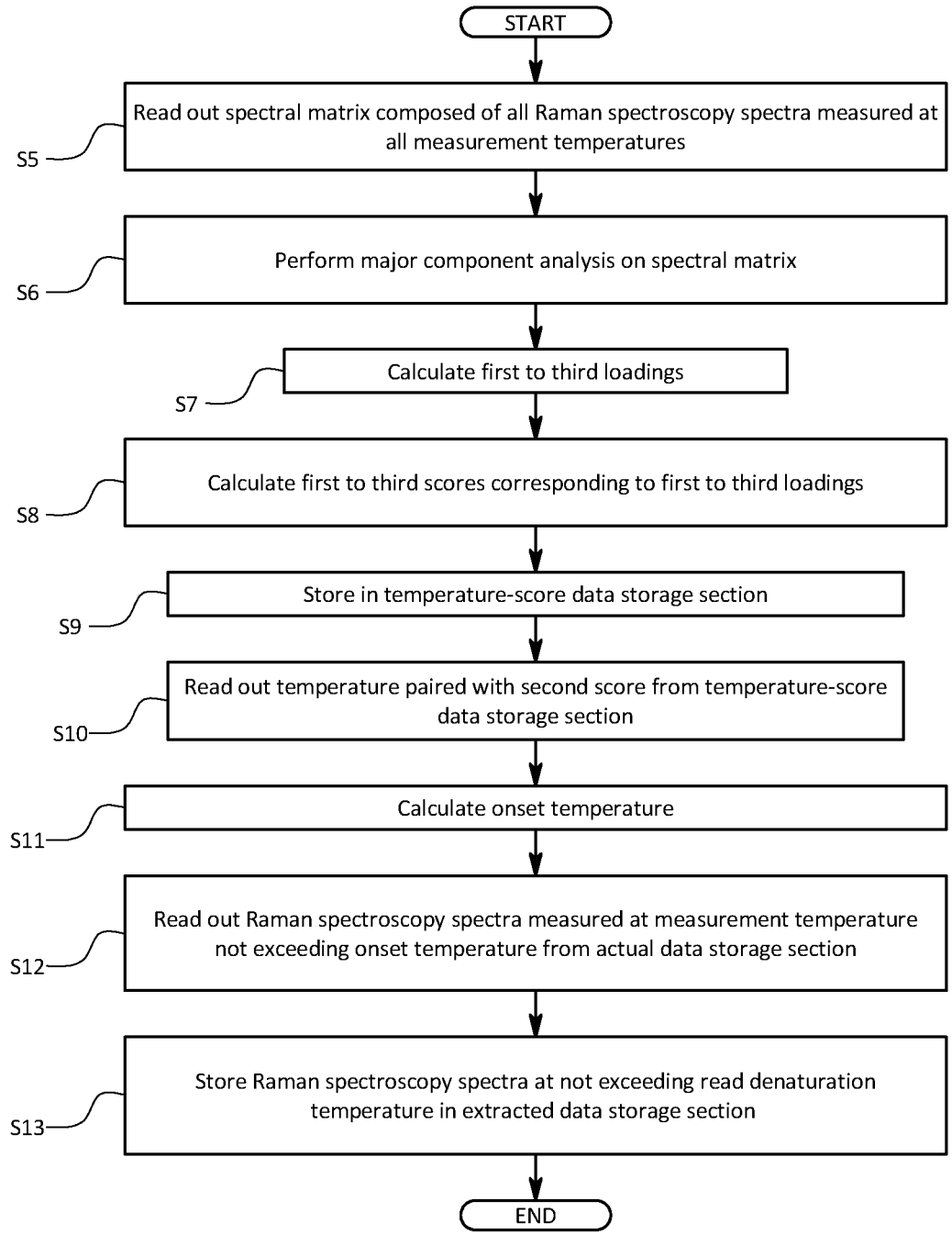
FIG. 8 is a schematic diagram illustrating a calculation procedure for a temporary denaturation temperature in the first embodiment.
Figure 9:
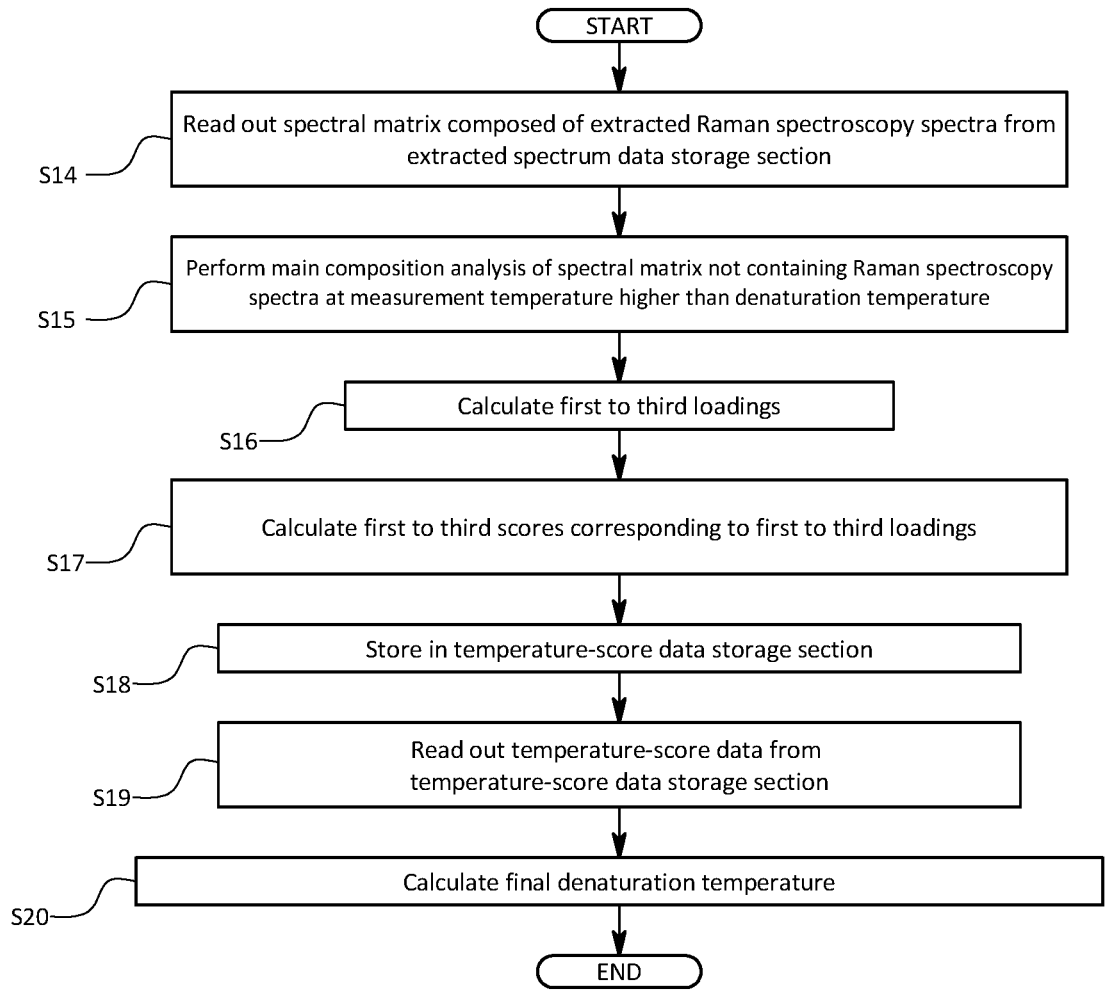
FIG. 9 is a schematic diagram illustrating a calculation procedure for a final denaturation temperature in the first embodiment.

Operations of the organic compound analysis system 200 thus configured are described with reference to flowcharts in FIGS. 7 to 9. FIG. 7 is the flowchart illustrating operations of the measuring apparatus 101 for the purpose of creating actual measured data. FIG. 8 is the flowchart illustrating operations of the organic compound analyzer 100 during which an onset temperature based on the second score for obtaining extracted data is obtained through PCA on the basis of actual measured data. FIG. 9 is the flowchart illustrating operations of the organic compound analyzer 100 during which a denaturation temperature of a minute structure due to a temperature change occurred in an antibody is calculated through PCA on the basis of the extracted data.

As illustrated in FIG. 7, the controller of the measuring apparatus 101 causes the heater 11 to raise a temperature of a sample W so as to reach a predetermined measurement temperature T(N) (step S1). The controller 15 then causes the light source 12 to emit laser light so that Raman scattering light is generated in the sample W. The Raman scattering light generated in the sample W is split by the spectroscope 13 and detected by the detector 14. Output of the detector 14 is measured as a Raman scattering spectrum composed of a Raman shift and information about measured Raman spectrum intensity (step S2). The measured Raman scattering spectrum is paired with the measurement temperature T(N) and transmitted to and stored in the actual measured data storage section 2 of the organic compound analyzer 100 as actual measured data (step S3). Thereafter, a determination is made as to whether a temperature of the sample W reaches a predetermined terminal temperature T(N) (step S4). Steps S1 to S4 are repeated when it does not reach the terminal temperature. When measurements of Raman spectroscopy spectra at all measurement temperatures by the measuring apparatus 101 are thus completed to store a sufficient amount of data in the actual measured data storage section 2, the organic compound analyzer 100 starts analysis by PCA.

As illustrated in FIG. 8, with the organic compound analyzer 100, a spectral matrix composed of all Raman spectroscopy spectra measured at individual measurement temperatures is firstly read out of the actual measured data storage section 2 (step S5). Then, PCA is performed on the read spectral matrix by the evaluation criterion vector setting section 3 and the score calculation section 4 (step S6). Firstly, the first to third PCA loadings are calculated as an inherent vector of variance-covariance matrix calculated from the spectral matrix read out by an algorithm of the PCA by the evaluation criterion vector setting section 3 (step S7). Then, the first to third scores are calculated by multiplying each of the first to third PCA loadings in order from right by the spectral matrix being read out (step S8). The calculated first to third scores are stored in the temperature-score data storage section 51 by being associated with measurement temperatures T(1) to T(N) in order with respect to values in the first row to the N-th row (step S9).

When the calculations of scores of Raman scattering spectra at all the measurement temperatures are completed and stored in the temperature-score data storage section 51, the onset temperature calculation section 52 reads out a temperature corresponding to the second score from the temperature-score data storage section 51 (step S10), and calculates an onset temperature by searching a temperature at which a component whose denaturation is completed starts to increase, for example, a point at which a change rate varies by a predetermined value or more. An index of measurement temperatures equivalent to the onset temperature is calculated (step S11), and the data extraction section 53 extracts a Raman scattering spectrum measured at a lower temperature than the onset temperature from the actual measured data storage section 2 (step S12) so as to be stored in the extracted data storage section (step S13).

The organic compound analyzer 100 is further that is configured to perform PCA on a spectral matrix composed only of Raman scattering spectra which are extracted in step S13 and measured while a minute structural change is occurring in the antibody, thereby calculating a terminal denaturation temperature as illustrated in FIG. 9. That is, processing similar to steps S5 to S9 is repeated on extracted data read out of the extracted data storage section 54 in steps S14 to S18. Finally, the denaturation temperature output section 55 reads out temperature-score data containing the third score from the temperature-score data storage section 51 (step S19), and a denaturation temperature is calculated on the basis of a temperature change in the third score, thus completing the analysis (step S20).

With the organic compound analysis system 200 and the organic compound analyzer 100 thus configured in the first embodiment, the denaturation temperature can be calculated taking into consideration information not only about a wavenumber of a peak, but also about spectrum intensities in the entire wavenumber region in the Raman spectroscopy spectra measured by PCA. This makes it possible to acquire information about the minute structural change overlooked in anywhere other than the peak, thereby reflecting the information on calculation accuracy of denaturation temperature.

Even when it is difficult to clearly observe a change in the Raman scattering spectrum derived from a structural change occurred in the antibody due to a temperature change during execution of the PCA, it is possible to suitably set the loading on which the change is reflected. It is therefore unnecessary to acquire a Raman spectroscopy spectrum serving as a model of a structure that is a desired measurement object by carrying out a preliminary experiment or the like.

Moreover, the use of the Raman scattering spectrum makes it possible to sufficiently obtain spectrum intensity necessary for analysis even when the sample W has a high concentration.

These lead to highly accurate calculation of a denaturation temperature derived from a micro structural change in the early stage of thermal denaturation. It is therefore possible to achieve analysis of the minute structural change occurred in the antibody in the antibody drug due to the temperature change, on the basis of the denaturation temperature.

An organic compound analyzer 100 in a second embodiment is described below.

The organic compound analyzer 100 in the second embodiment is different from the organic compound analyzer 100 in the first embodiment in that infrared absorption spectrum is used as a spectrum for calculating a denaturation temperature, and in that the evaluation criterion vector spectrum setting section 3 sets an evaluation criterion vector on the basis of a known model spectrum instead of PCA. For example, other spectra whose number is equal to the number of measurement points being measured as an actual measured spectrum are set as an evaluation criterion vector. Even by doing so, it is possible to highly accurately calculate a denaturation temperature on which a minute structural change of protein is reflected along with a temperature change by using information about spectrum intensity in anywhere other than a peak. Alternatively, various spectra obtainable from protein, such as fluorescence spectrum and CD spectrum besides the infrared absorption spectrum, may be measured at a plurality of measurement temperatures, and a denaturation temperature may be obtained from a spectral matrix thereof.

Other embodiments are described below.

An object whose denaturation temperature is measured is not limited to an antibody in the present invention, and the object may be protein. Algorithms for calculating loadings and scores are not limited to PCA. For example, in order to avoid preparation of a model spectrum, it is necessary to use algorithms, such as CA, NLM, kNN, and MCR. When preparing a model spectrum, it is possible to use algorithms, such as MLR, PCR, PLS, NN, and LDA.

The evaluation criterion vector setting section and the score calculation section may be that is configured to calculate only a measurement object. For example, the organic compound analyzer may be configured to calculate only the second PCA loading and the second score, or only the third PCA loading and the third score. Instead of the first embodiment with which a denaturation temperature is calculated using extracted data obtained by extracting a part of actual measured data, the denaturation temperature may be calculated directly from actual measured data. Depending on the kind of protein and the kind of antibody, it may be unstable whether a change in score derived from a minute structure in the early stage of denaturation occurs in either one of the second score and the third score. Therefore, a score used for measuring an onset temperature and a denaturation temperature may be suitably selected either one of the second score and the third score, or alternatively a different score, such as a fourth score, may be used.

Although the spectrum measurement object is protein in the above embodiments, the object may be any organic compound other than protein. For example, biospecimens and amino acids may be employed as an organic compound. There is no intention to limit external stimulus conditions to temperatures, and it is therefore possible to employ other parameters. For example, when focusing on the denaturation of protein, each of spectra needs to be measured by changing external stimulus condition, such as concentration of a solute added to a sample, pH and presence time of the sample in an interface. Specific examples of the solute, which causes denaturation by being added to protein, include guanidine salt and urea. In this case, the change feature point determination section needs to be configured to determine, as a change feature point, a midpoint concentration between a concentration at which a score starts to change in response to concentration changes in the solute, and a concentration at which the change in the score is terminated. When the protein is denatured by changing pH, a point at which a score starts to change in response to changes in concentration of hydrochloric acid and sodium hydroxide added to the sample, and a change in pH itself, and a point at which the score is terminated need to be searched, and a midpoint between the two points needs to be determined as a change feature point. When protein being a sample is present in a gas-liquid interface and a solid-liquid interface, the protein itself may act as a surface active agent, and the protein itself may be denatured. In this case, a change feature point may be determined on the basis of changes in score in response to time during which the protein is allowed to stay in the interface. There is no intention to limit the method of determining a change feature point to those described in the above embodiments. For example, a point at which a change in score starts to occur may be used as a change feature point, and a point at which the change in score is terminated may be determined as a change feature point.

The evaluation criterion vector may be set with various methods without limiting to those described in the above embodiments. In regard to scores, instead of directly calculating an inner product of a spectrum and an evaluation criterion vector, it is possible to perform individual calculations or such a calculation that results in the same value as the inner product.

Other various modifications and combinations of the embodiments may be made without departing from the spirit and scope of the present invention.

INDUSTRIAL APPLICABILITY

The present invention is capable of providing the organic compound analyzer making it possible to highly accurately determine, for example, a thermal denaturation temperature on which a minute structural change in the early stage of thermal denaturation of protein is reflected.

What is claimed is:

1. An organic compound analyzer comprising:
    an actual measured data storage section that is configured to store in pairs a plurality of actual measured Raman spectroscopy spectra obtained through measurement of a sample containing an organic compound under a plurality of different external stimulus conditions, wherein the sample is an antibody drug and the organic compound is an antibody;
    an evaluation criterion vector setting section that is configured to set an evaluation criterion vector having a number of elements equal to a number of measurement points for a wavenumber at which spectrum intensity of the actual measured Raman spectroscopy spectra is measured;
    a score calculation section that is configured to calculate scores based on an inner product of the actual measured Raman spectroscopy spectra and the evaluation criterion vector with respect to a plurality of external stimulus conditions; and
    a change feature point determination section that is configured to determine a change feature point of the antibody on a basis of a change in the scores with respect to external stimulus conditions, wherein
    the evaluation criterion vector setting section is configured to set the evaluation criterion vector by calculating loadings having at least second and third contribution rates, and
    the score calculation section is configured to calculate the scores corresponding to the loadings having the second and third contribution rates, with respect to external stimulus conditions, and to determine a change feature point due to a minute structural change in an early stage of denaturation that occurs in the antibody based on a change in the scores corresponding to the loadings having the second and third contribution rates.

2. The organic compound analyzer according to claim 1, wherein the evaluation criterion vector setting section is configured to set the evaluation criterion vector by performing multivariate analysis of a spectral matrix composed of a plurality of actual measured Raman spectroscopy spectra measured under a plurality of different external stimulus conditions.

3. The organic compound analyzer according to claim 1, wherein
    the loadings calculated by the evaluation criterion vector setting section are PCA loadings,
    the evaluation criterion vector setting section is configured to set the evaluation criterion vector by calculating the PCA loadings on a basis of a spectral matrix composed of a plurality of actual measured Raman spectroscopy spectra measured under a plurality of different external stimulus conditions, and
    the score calculation section is configured to calculate the scores as a product of the spectral matrix and each of the PCA loadings under a plurality of external stimulus conditions.

4. The organic compound analyzer according to claim 3, wherein
    the evaluation criterion vector setting section is configured to set the evaluation criterion vector by calculating the PCA loadings having second and subsequent contribution rates on a basis of the spectral matrix.

5. The organic compound analyzer according to claim 1, wherein
    the evaluation criterion vector setting section is configured to set the evaluation criterion vector on a basis of a known spectrum of an antibody, and
    the score calculation section is configured to calculate a product of a spectral matrix composed of a plurality of actual measured Raman spectroscopy spectra measured under a plurality of different external stimulus conditions and the evaluation criterion vector, as the scores under a plurality of external stimulus conditions.

6. The organic compound analyzer according to claim 1, wherein the external stimulus conditions are either one of a concentration of a solute added to a sample, a pH, existence time of the antibody drug in an interface, and a temperature.

7. The organic compound analyzer according to claim 1, wherein, when the external stimulation conditions are temperatures,
    the change feature point determination section comprises;
        an onset temperature calculation section that is configured to calculate an onset temperature at which a component in which denaturation of the antibody is already completed starts to occur, on a basis of a change in the score with respect to a temperature which is calculated from a plurality of the actual measured Raman spectroscopy spectra;
        a data extraction section that is configured to extract, from the actual measured data storage section, an actual measured spectrum measured at a lower temperature than the onset temperature; and
        a denaturation temperature output section that is configured to calculate a denaturation temperature being a change feature point on a basis of a change in the scores with respect to a temperature which is calculated by the score calculation section on a basis of actual measured data extracted by the data extraction section.

8. An organic compound analysis method intended to analyze an organic compound on a basis of a plurality of actual measured Raman spectroscopy spectra obtained through measurement of a sample containing an organic compound under a plurality of different external stimulus conditions, wherein the sample is an antibody drug and the organic compound is an antibody, the method comprising:
- an evaluation criterion vector setting step of setting an evaluation criterion vector having a number of elements equal to a number of measurement points for a wavenumber at which spectrum intensity of the actual measured Raman spectroscopy spectra is measured;
- a score calculation step of calculating scores based on an inner product of the actual measured Raman spectroscopy spectra and the evaluation criterion vector with respect to a plurality of external stimulus conditions; and
- a change feature point determination step of determining a change feature point of the antibody on a basis of a change in the score with respect to external stimulus conditions, wherein the evaluation criterion vector setting step includes setting the evaluation criterion vector by calculating loadings having at least second and third contribution rates, and the score calculation step includes calculating the scores corresponding to the loadings having the second and third contribution rates, with respect to external stimulus conditions, and determining a change feature point due to a minute structural change in an early stage of denaturation that occurs in the antibody based on a change in the scores corresponding to the loadings having the second and third contribution rates.

9. A non-transitory computer readable medium storing a program for an organic compound analyzer causing a computer to execute steps comprising:
- an evaluation criterion vector setting of setting an evaluation criterion vector having a number of elements equal to a number of measurement points for a wavenumber at which spectrum intensity of an actual measured Raman spectroscopy spectra is measured, the actual measured Raman spectroscopy spectra being one of a plurality of actual measured Raman spectroscopy spectra obtained through measurement of a sample containing an organic compound under a plurality of different external stimulus conditions, wherein the sample is an antibody drug and the organic compound is an antibody;
- a score calculation step of calculating scores based on an inner product of the actual measured Raman spectroscopy spectra and the evaluation criterion vector with respect to a plurality of external stimulus conditions; and
- a change feature point determination step of determining a change feature point of the antibody on a basis of a change in the scores with respect to external stimulus conditions, wherein the evaluation criterion vector setting step includes setting the evaluation criterion vector by calculating loadings having at least second and third contribution rates, and the score calculation step includes calculating the scores corresponding to the loadings having the second and third contribution rates, with respect to external stimulus conditions, and determining a change feature point due to a minute structural change in an early stage of denaturation that occurs in the antibody based on a change in the scores corresponding to the loadings having the second and third contribution rates.

* * * * *